United States Patent [19]
Keeling et al.

[11] Patent Number: 5,476,444
[45] Date of Patent: Dec. 19, 1995

[54] SPECIALIZED PERFUSION PROTOCOL FOR WHOLE-BODY HYPERTHERMIA

[75] Inventors: Norman G. Keeling, McMurray, Pa.; Stephen R. Ash; Robert B. Truitt, both of Lafayette, Ind.; Joseph A. Guzman, Atlanta, Ga.

[73] Assignee: IDT, Inc., Pittsburgh, Pa.

[21] Appl. No.: 318,132

[22] Filed: Oct. 4, 1994

Related U.S. Application Data

[63] Continuation-in-part of Ser. No. 940,546, Sep. 4, 1992, Pat. No. 5,354,277.

[51] Int. Cl.$^6$ .................................................. A61M 1/03
[52] U.S. Cl. ............................... 604/4; 604/6; 604/5
[58] Field of Search .......................... 604/4, 5, 6, 19, 604/27, 28, 113, 114

[56] References Cited

U.S. PATENT DOCUMENTS

| | | | |
|---|---|---|---|
| 2,886,771 | 5/1959 | Vincent | 324/30 |
| 3,482,575 | 12/1969 | Claff et al. | 128/214 |
| 4,061,141 | 12/1977 | Hyden et al. | 128/214 |
| 4,191,182 | 3/1980 | Popovich et al. | 128/214 |
| 4,321,918 | 3/1982 | Clark, II | 128/214 |
| 4,322,275 | 3/1982 | Jain | 204/180 |
| 4,381,004 | 4/1983 | Babb | 128/214 |
| 4,479,798 | 10/1984 | Parks | 604/175 |
| 4,540,401 | 9/1985 | Marten | 604/28 |
| 4,563,170 | 1/1986 | Aigner | 604/5 |
| 4,576,143 | 3/1986 | Clark, III | 128/1 R |
| 4,692,138 | 9/1987 | Troutner et al. | 604/4 |
| 4,787,883 | 11/1988 | Kroyer | 604/4 |
| 4,808,189 | 2/1989 | Wilson | 604/4 |
| 4,950,225 | 8/1990 | Davidner et al. | 604/4 |

OTHER PUBLICATIONS

DeMoss, J. L. et al., "Hyperthermia in the Treatment of Cancer", 1985, vol. 17, No. 1, pp. 37–43.
Sanchez, R. et al., "Overview of Whole Body Hyperthermia Experience at American International Hospital", 1990, pp. 203–208.
Levin, R. D. et al., "Whole Body Hyperthermia Experience in Breast Cancer at American International Hospital", 1990, pp. 387–391.
Perez, C. A. et al., "Randomized Phase III Study Comparing Irradiation and Hyperthermia with Irradiation Alone in Superficial Measurable Tumors", Am J Clin Oncol (CCT) 14(2) 1991, pp. 133–141.
O'Malley, S. "Hyperthermia: Perfusion's Answer to AIDS?", Jan. 1991, pp. 6–13.
Logan, W. D. et al., "Case Report: Total Body Hyperthermia in the Treatment of Kaposi's Sarcoma in an HIV Positive Patient", 1990, pp. 45–47.
James, J. S., "Hyperthermia Report: Only One Patient", AIDS Treatment News, Issue No. 104 Jun. 1, 1990, pp. 1–2.
Yatvin, M. B., "An Approach to AIDS Therapy Using Hyperthermia and Membrane Modification", Medical Hypotheses (1988) 27, 1988, pp. 163–165.

*Primary Examiner*—Sam Rimell
*Attorney, Agent, or Firm*—Webb Ziesenheim Bruening Logsdon Orkin & Hanson

[57] ABSTRACT

A method for extracorporeal blood heating to effect whole body hyperthermia, which utilizes a hemodialyzer with a sorbent suspension in the dialysate, a blood pump and a heat exchanger—in addition to various probes and catheters and heated anterior and posterior blankets for the patient—to effect extracorporeal treatment without adverse effect on blood physiology and without the need for general anesthesia. Blood returning to the body is heated to at least about 46° C. Incorporation of hemodialysis into the blood heating treatment solves at once several problems which plagued prior art hyperthermia techniques: it rectifies any imbalances of sodium, potassium, magnesium, bicarbonate or phosphate, and may remove toxins incident to necrosis of tumors and virally infected cells. Hyperthermia protocols with sorbent—based dialysis of blood thus avoid the various serious side effects which complicated—even to the point of death—the hyperthermia treatments known from the past.

15 Claims, 1 Drawing Sheet

SPECIALIZED PERFUSION PROTOCOL FOR WHOLE-BODY HYPERTHERMIA

CONTINUATION-IN-PART INFORMATION

The following specification is a Continuation-in-Part of U.S. application Ser. No. 07/940,546, filed Sep. 4, 1992 U.S. Pat. No. 5,354,277.

FIELD OF THE INVENTION

The present invention relates to a specialized method for whole-body hyperthermia, including extracorporeal blood heating and dialysis, as an antiviral protocol.

BACKGROUND OF THE INVENTION

Hyperthermia as a treatment of tumors has been carefully studied and applied since the 1960's. Prior to that period there were multiple reports of tumor regression coincident with episodes of fever. Biochemical analysis of the effects of hyperthermia has indicated that temperatures greater than 41° C. generally are needed to induce tumor necrosis (tumor death). Although there are multiple methods of inducing hyperthermia including paraffin wax baths, a heat chamber and a water blanket, many physicians now favor an extracorporeal heat exchange (blood) circuit when whole body heating is the goal. Patients may be maintained at 41.5° to 42° C. (core body temperature) for three to four hours without severe compromise of cardiovascular function, although some physicians have reported elevation of serum transaminases and bilirubin in patients kept at these temperatures for greater than 10 to 40 minutes. Instances of neurologic damage have been reported in association with serum hypophosphatemia, although no significant problems occurred once phosphate levels were maintained. Deaths have also been reported in two patients receiving hyperthermia at 41.5° to 42° C. for 1½ to 2 hours, presumably from massive tumor necrosis, particularly in the liver.

DeMoss, J. L. et al., "Hyperthermia in the Treatment of Cancer," *The Journal of Extra-Corporeal Technology*, Vol. 17, No. 1, pp. 37-43, 1985, explains how tumors are vulnerable to externally applied heat and that the goal of hyperthermic treatment therapy is to achieve cytotoxic temperatures in the tumor for a sufficient length of time without damaging the surrounding normal tissue. The rate at which blood flows through any given area of tissue determines the amount of heat that may be carried away and therefore is a major determinant of the temperature rise in that tissue. In normal tissue, heat causes vasodilation. In a tumor, the microvasculature is made up of an overabundance of capillary beds which are unable to dilate. Blood flow through the area is thus more sluggish and commensurately unable to dissipate heat applied to the area. The inability to respond to heat by dilation, as normal vasculature would, also subjects the tumor to hypoxia, anaerobic metabolism and local acidosis; these conditions in turn make the tumor tissue more vulnerable to thermal injury. Conversely, when extracorporeal heating is used to create hyperthermia, the inability of tumor vasculature to constrict results in higher temperature and more cellular damage.

Other literature addressing the utility of hyperthermia in the treatment of malignancy includes: Sanchez, R., "Overview of Whole Body Hyperthermia Experience at American International Hospital," *Consensus on Hyperthermia for the* 1990's, Plenum Press, New York, pp. 203-208 (1990); Levin, R. D. et al., "Whole Body Hyperthermia Experience in Breast Cancer at American International Hospital," *Consensus on Hyperthermia for the* 1990s, Plenum Press, New York, pp. 387-391 (1990); Perez, C. A. et al., "Randomized Phase III Study Comparing Irradiation and Hyperthermia with Irradiation Alone in Superficial Measurable Tumors," *Am. J. Clin. Oncol.*, Vol. 14, no. 2, pp. 133-141 (1991); and others.

Patents relating to methods for the extracorporeal treatment of blood for cancers, viruses and parasites include U.S. Pat. Nos. 2,886,771 to Vincent, 3,482,575 to Claff, 4,061, 141 to Hyden, 4,191,182 to Popovich, 4,321,918 to Clark, 4,322,275 to Jain, 4,381,004 to Babb, 4,479,798 to Parks, 4,540,401 to Marten, 4,563,170 to Aigner, 4,576,143 to Clark and 4,692,138 to Troutner et al.

There were two reasons for exploring the use of hyperthermia as a treatment for viral-associated neoplasms when such work began a few years ago. First, hyperthermia was known to have caused tumor regression in both animal and in human sarcomas. Studies on the biochemical and physiologic effects of hyperthermia had shown that damage to microvasculature is important for tissue necrosis associated with heat. Second, the human lymphadenopathy associated virus was known to be heat-sensitive. McDougal et al. incubated lymphadenopathy associated virus at temperatures ranging from 37° to 60° C. and found the log kill followed first order kinetics. Thermal inactivation was decreased when the virus was in the lyophilized state compared to the liquid state (10 fold loss in LD50 121 seconds at 56° C. for virus in media versus 32 minutes in lyophilized state). It was also found that lymphadenopathy virus was 40% inactivated after 30 minutes in a 42° C. waterbath, and 100% inactivated after the same time period at 56° C. Thus, hyperthermia can benefit patients suffering from viral infections in two ways. First, the hyperthermia kills malignant cells in the viral-associated neoplasms. Second, the hyperthermia directly inactivates the viruses themselves by denaturing them.

Studies have previously been completed in which whole body hyperthermia, achieved via extracorporeal heating of blood, was used to treat Kaposi's Sarcoma associated with human immunodeficiency virus infection. While evaluation of the therapeutic effects of such treatment on Kaposi's sarcoma was the primary purpose of these studies, the simultaneous effects on HIV disease were evaluated by studying immunologic and virologic parameters of HIV infection.

The use of hyperthermia in acquired immunodeficiency syndrome patients with Kaposi's Sarcoma has received considerable public and media attention. After treatment of the first two patients upon whom this procedure was performed, the treating physicians requested that the National Institute of Allergy and Infectious Diseases (NIAID) evaluate the study techniques, results and patients.

As reported in O'Malley, S., "Hyperthermia: Perfusion's Answer . . . ?", *Perfusion Life*, January 1991, pp 6-13, a patient named Carl Crawford experienced a dramatic recovery from head-to-toe skin cancers after being treated with extracorporeal blood heating. (This case study was published in Logan, W. D. et al., "Case Report: Total Body Hyperthermia in the Treatment of Kaposi's Sarcoma . . . ," *Med. Oncol. & Tumor Pharmacother.*, vol. 8, no. 1, pp. 45-47 (1991).) Mr. Crawford had been diagnosed as having Kaposi's Sarcoma incident to human immunodeficiency virus infection, and had been told he had only two to four weeks left to live. Mr. Crawford was the first patient whose blood was heated to create a core temperature of 42° degrees C. which, the doctors said, killed the cells infected with human immunodeficiency virus. Although NIAID discounted Mr. Crawford's recovery due to an alleged error in diagnosis—NIAID maintained that Mr. Crawford never had Kaposi's Sarcoma but had cat—scratch fever instead—several other doctors besides the treating physicians had diagnosed Mr. Crawford's skin lesions as Kaposi's Sarcoma. Growing numbers of physicians are convinced that hyperthermia provides a proven antiviral protocol. For example, Dr. Robert S. Jenkins, Medical Director of the Immuno Suppressed Unit at Hollywood Community Hospital, believes that the hyperthermia was responsible for curing Mr. Crawford's Kaposi's Sarcoma lesions.

In a completely separate effort, Dr. Shawn Hankins, a chiropractor in Port Angeles, Wash., has supported hyperthermia treatments since July, 1987 (as explained in the *Acquired Immunodeficiency Syndrome Treatment News*, Issue No. 104, Jun. 1, 1990, page 2). (He points out that human immunodeficiency virus is heat-sensitive and, in addition, hyperthermia can cause increased T-cell proliferation, phagocytosis, and increased production of antibodies and interferon. Observations of phenomenon such as the "honeymoon effect" that sometimes follows pneumocystitis (which causes a high fever) also support this conclusion.)

Other publications directed generally toward the treating of human immunodeficiency virus with heat include: Weatherburn, H., "Hyperthermia . . . ," *The British Journal of Radiology*, Vol. 61, no. 729, pp. 863–864 (1988); Yatvin, M. B.,"An Approach . . . Using Hyperthermia and Membrane Modification," *Medical Hypotheses*, Vol 27, pp. 163–165 (1988); and U.S. Pat. No. 4,950,225 to Davidner et al., "Method for Extracorporeal Blood Shear Treatment."

The latter, Davidner et al., discusses the extracorporeal treatment of the blood of a human immunodeficiency virus patient with a) hyperthermia; b) mechanical shear and/or c) irradiation. When hyperthermia is used, the blood is heated to between 41.0° and 42.5° C. (or somewhat higher), and pH is adjusted by adding sodium bicarbonate intravenously when necessary. Blood is held under low flow or static conditions, extracorporeally, so that the blood treatment or treatments are (assertedly) maximally successful in ineffectuating the human immunodeficiency virus.

Among the known protocols for extracorporeal heating of blood, various difficulties persist, including (as outlined above) elevated serum transaminases and bilirubin, instances of neurologic damage associated with serum hypophosphatemia, risk due to abnormal pH or to abnormal sodium, sodium bicarbonate or potassium levels, and possible death from massive tumor necrosis. A need therefore remains for a more reliable, simpler and more comprehensive extracorporeal hyperthermia treatment method in which unwanted side effects are reduced or eliminated altogether.

SUMMARY OF THE INVENTION

The present invention is a method for extracorporeal blood heating to effect whole body hyperthermia, which utilizes a hemodialyzer with sorbent suspension in dialysate, a blood pump and a heat exchanger—in addition to various probes and catheters and heated anterior and posterior blankets for the patient—to effect extracorporeal treatment without adverse effect on blood physiology and without the need for general anesthesia. Blood returning to the body is heated to about 46° C. Incorporation of hemodialysis into the blood heating treatment solves at once several problems which plagued prior art hyperthermia protocols: it rectifies any imbalances of sodium, potassium, magnesium, bicarbonate, or phosphate, and may remove toxins incident to necrosis of tumors and virally infected cells. Hyperthermia protocols with sorbent-based dialysis of blood avoid the various serious side effects which complicated—sometimes even to the point of death—the hyperthermia treatments known from the past.

DETAILED DESCRIPTION OF THE INVENTION

Figure 1:
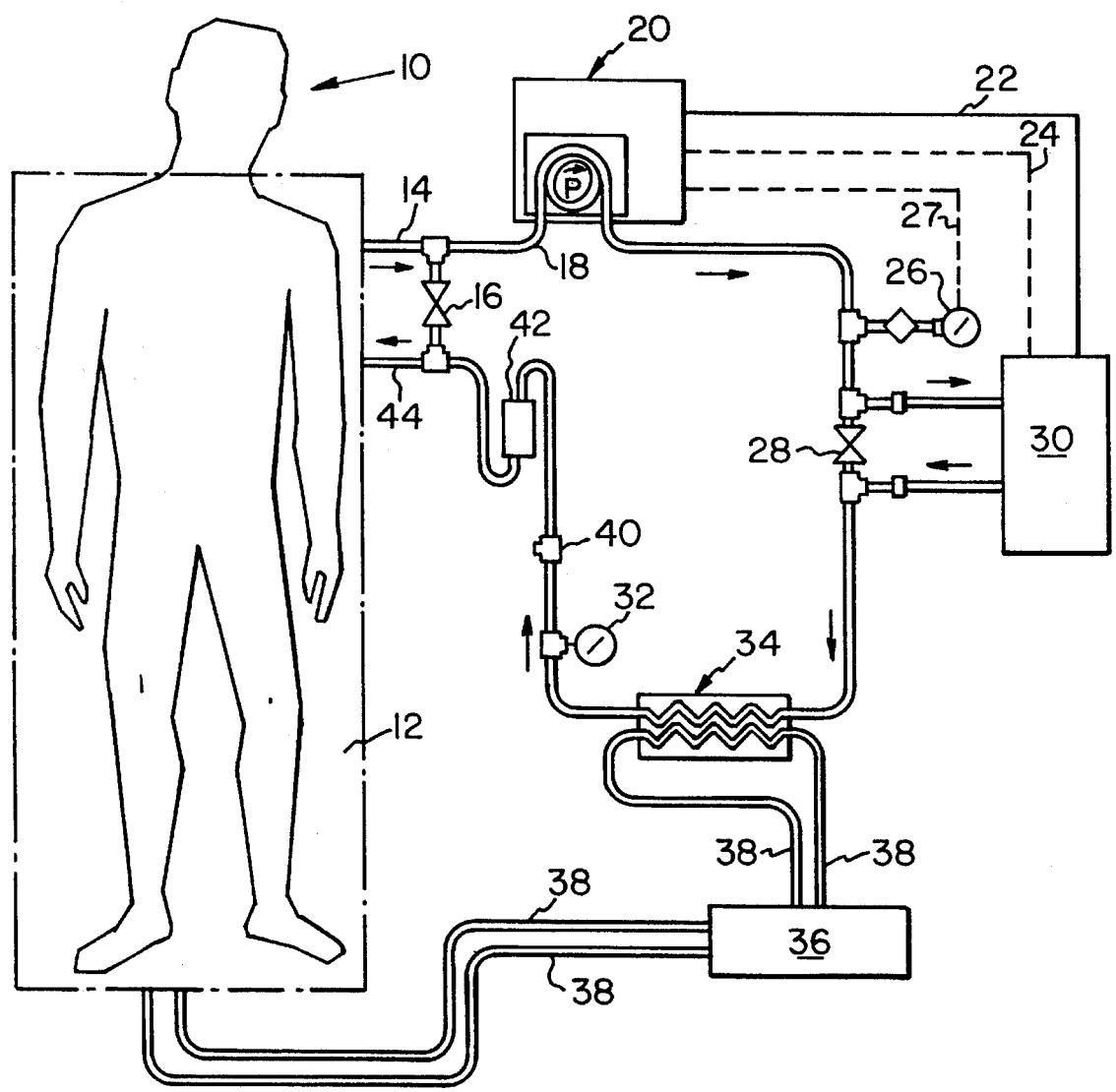
FIG. 1 is a schematic illustration of a combination of devices used to effect a preferred embodiment of the present hyperthermia technique.

The present invention is a method for extracorporeal blood treatment which utilizes a hemodialyzer, a blood pump, and a heat exchanger—in addition to various probes and catheters and heated anterior and posterior blankets for the patient—to effect extracorporeal treatment without adverse effect on blood physiology and without the need for general anesthesia. Incorporation of hemodialysis into the blood heating treatment rectifies any imbalances of sodium, potassium, bicarbonate, or phosphate, and removes any toxins incident to necrosis of any tumors or virally-infected cells.

The technique itself can be summarized as follows. After amnesiacs and analgesics or other sedation (typically not general anesthesia for the patient's sake) are given to the patient, an Impra double-lumen catheter (or smaller or larger arterial or venous catheters or equivalent structure(s)) is placed—by catheter placement techniques known in the art including local anesthesia—in the jugular, subclavian or femoral vein (whichever is most accessible for any given patient). Heparinization is effected only upon initial catheterization at a level of approximately 2.4 mg. per kilogram patient body weight. A heating-cooling mattress is positioned under the patient, and a heating-cooling blanket over the patient, to assist in effecting whole-body hyperthermia. A hemodialyzer is incorporated into the extracorporeal blood "Circuit"; the circuit also contains a blood pump, a heat exchanger and, most preferably, a primary blood heater, for rapid control of the patient's body temperature. When all these devices are used and when the blood returning to the patient is heated to at least about 46° C., preferably about 48° C., the desired core body temperature of about 42° C. (41°–42.5° C., more preferably 41.5°–42° C.) is reached in about 40 to 50 minutes. This elevated body temperature is maintained for about 1 or 2 hours, and cooling is subsequently effected over a period of 20 to 40 minutes. During the procedure, the patient is monitored for pulmonary artery pressure, radial artery pressure and pulmonary artery and bladder temperature. After 1 or 2 hours, the patient is cooled to between 38° and 39° C. and extracorporeal blood circulation is ended.

According to one embodiment of the invention, after placement of the catheter, the blood flows through 1) a hemodialyzer; 2) a blood pump; 3) a tubular heat exchanger and 4) a stopcock for collecting and/or monitoring the extracorporeal blood, prior to return of circulation through the same catheter; and 5) associated other optional control structures including temperature and pressure sensors and air filters (which remove any air emboli which may be circulating in the system). The patient should rest on and be covered by heating/cooling mattresses/blankets to allow the practitioner to augment blood heating with direct body heating, to facilitate the raising of the core body temperature.

All of the above equipment is well-known in the art and only minor modifications are required prior to its use in the present process. The hemodialyzer should be modified to allow the temperature of the dialyzing fluid to be maintained at up to 48° C., something hemodialyzers have previously not typically been designed to do. Notwithstanding this, however, modifying a hemodialyzer to provide controlled heat to the dialyzing fluid is a simple mechanical modification well within the ordinary skill of the art. The heat exchanger is included in the system to confer (or remove) additional heat beyond that provided by the heated dialyzing fluids. Heating/cooling blankets/mattresses and their associated equipment (an entire system of these devices is available, for instance, from Cincinnati Sub-Zero Products, Inc.) may be used minor modification permitting a higher upper temperature limit.

Because of the patient's natural depletion of carbohydrate and fat stores, these substances should be administered during and/or after treatment to assure that these precursors are adequately available to marginally competent metabolic pathways. Hemodialysis maintains levels of phosphate and calcium during treatment—which levels would otherwise fall as a result of the hyperthermia—especially when acid/bicarbonated water is used as the dialyzing solution. Maintenance of arterial oxygen tensions as high as possible during hyperthermia by use of 100% oxygen for ventilation should satisfy the need to maintain greater than normal blood and tissue oxygen tensions necessitated by hyperthermia-increased oxygen consumption.

Blood flow rates should be between about 300–750 ml per minute when human patients are treated with the present whole-body hyperthermia technique.

Prior to treatment, patients are screened for underlying heart disease; underlying lung disease (including pulmonary Kaposi's Sarcoma if one or more lesions is greater than a certain size); pregnancy; a Karnofsky score of less than 60%; a non-correctable hematocrit of less than 30 ml; hemoglobin less than 10%; active opportunistic infection; bleeding disorders; or Diabetes Mellitus. Any of the foregoing warrants careful consideration of the risks versus the benefits of hyperthermia treatment, since an important consideration in the practice of the present technique is whether the patient can tolerate it. The prehyperthermia evaluation requires a routine history and physical examination, routine laboratory studies, chest x-rays, urinalysis, electrocardiogram and pulmonary function studies. Special studies include P-24 antigen level assay; reverse transcriptase assay; human immunodeficiency virus cultures; lymphocyte quantitative analysis and thyroid profile.

The present improved hyperthermia technique has application in every indication for which hyperthermia was indicated in the past, namely, to combat neoplasms and viral infections. Human clinical studies have already shown that hyperthermia is effective to treat (not necessarily to cure) viral infections including the retroviral infections such as Hepatitis B and human immunodeficiency viruses. That hyperthermia is effective in all these applications has already been established; the present invention inheres in the improvements to the preexisting hyperthermia methods and the way in which the improvements avoid the side effects ubiquitous in the prior art.

Unlike previously known whole-body hyperthermia techniques, the present protocol is not conducted using general anesthesia per se but is instead conducted using sedation. The use of sedative amounts—as distinct from anesthetic amounts—of thiopental sodium is preferred. With the patient sedated, but not unresponsive, central nervous system activity can readily be monitored during hyperthermia treatment.

The use of hemodialyzers, as well as the underlying technology of their manufacture, is well-known and well established in the medical arts. The various acid- and bicarbonate-containing dialyzing solutions available are also well-known; typical commercially available dialyzing solutions are Centrisol (Cobe) or Renasol (Fresenius). Much of dialysis technology is itself well understood, and therefore is not being repeated here. For the purpose of the present invention, the incorporation of dialysis into the extracorporeal blood surface is intended to accomplish the same blood "clean-up" as ordinary dialysis of a renally compromised patient would remove toxins of kidney failure. The dialysis procedure during hyperthermia allows many important electrolytes to be regulated (sodium, potassium, phosphate, calcium, magnesium and pH are all kept at appropriate levels in the blood) and in addition any toxins incident to death of virally infected cells and Kaposi's Sarcoma cells are filtered out. One part of the present invention is in the realization that adding hemodialysis to extracorporeal hyperthermia could maintain more normal blood chemistries. The other part is the development of a sorbent suspension to automatically create the dialysate concentrations to counteract changes in blood chemistry.

Although hemodialysis generally encompasses all known methods of dialysing the blood, a particular type of hemodialysis is contemplated as most preferred: sorbent-based hemodialysis. This preferred form of hemodialysis is described further below and in the examples, particularly Example 2. U.S. Pat. No. 5,277,820 to Ash discloses a sorbent-based hemodialysis method and apparatus, and this patent is hereby incorporated herein by reference. This hemodialysis technology resides in the use of a specialized sorbent (a sorbent suspension) as the hemodialysing solution, and the use of all types of sorbent preparations as dialysates is contemplated as a part of the present invention.

The sorbent suspension generally includes powdered surface adsorptive agents, ion exchangers, physiologic electrolytes and macromolecular flow inducing agents. In general, these components are present in effective amounts to achieve the desired removal of substances from the electrolyte balance in the blood of the patient while maintaining the stability and fluidity of the sorbent suspension. The powdered surface adsorptive agent is usually activated charcoal, preferably with an average particle diameter not exceeding about 74 microns. Even more preferably, the average particle diameter does not exceed 50 microns. Macromolecular flow inducing agents such as glycol derivatives help to maintain the flow properties and stability of the particle suspensions.

The sorbent suspensions also may include ion-exchange substances to bind ions, such as ammonia, which may appear in the patient's blood. Many suitable ion exchangers including polystyrene sulfonate and zeolite are known in the art. The ion-exchanger is preferably a cation-exchange resin, which is desirably loaded with sodium, calcium, magnesium, and some hydrogen. For example, to date, sodium polystyrene sulfonate has been a preferred cation exchange resin.

The surface adsorptive agent, electrolytes, flow inducing agents and any other additives will usually comprise about 5% to 30% by weight of the sorbent suspension formulation as a whole, with the remainder being water. Typically, solid sorbents will comprise about 2% to 25% by weight of the suspension formulation, and electrolytes will comprise about 1% to 5% of the suspension formulation. Within these parameters, more preferred sorbent suspension formulations comprise about 2% to 20% powdered surface adsorptive agent, up to about 10% ion-exchanger, and up to about 1% flow agent such as a pluronic and/or polyvinylpyrrolidone (PVP).

There are many dialyzer membranes which are known for use in dialysing body fluids such as blood, and these membranes may be used with the sorbent suspension as though the sorbent suspension were a simple dialysis solution. One suitable membrane of this type is a cellulosic membrane composed of regenerated cuproammonium cellulose (Cuprophan®).

Sorbent suspensions as described above are advantageously used in a dialysis instrument including a parallel plate dialyzer, by moving the sorbent suspension formulation in a counter-current mode by the direct application of alternating negative pressure and positive pressure on the dialysate side. Back and forth movement of the membrane not only propels blood through the dialyzer but mixes sorbent suspension at the membrane surface.

The sorbent suspension works as follows. When blood opposes the sorbent suspension, separated only by the dialysis membrane, diffusion causes many chemicals to pass from the blood into the sorbent suspension on the other side of the membrane. Depending upon the binding characteristics of the sorbents, some chemicals remain at low concentration in the sorbent suspension (and are therefore efficiently removed from the blood) and others reach concentrations similar to the blood (and are therefore not removed from the blood). Inclusion of certain chemicals in the sorbent suspension composition can partially saturate sorbent binding sites or create precipitates which can return chemicals to the blood during treatment. Thus, the sorbent suspension may be tailored to remove very specific compounds from the blood, without removing others.

When the above-described sorbent suspensions are used in hyperthermia treatments, the following adaptations of the disclosure of U.S. Pat. No. 5,277,820 are typical. Although the same cation exchangers are used in sorbent-based hemodialysis without hyperthermia, the cation exchangers are generally heavily loaded with Ca, K and Mg ions at the start of hyperthermia (in an amount to be in equilibrium with the normal blood concentration of these cations). Also, for control of blood phosphate concentration during hyperthermic treatments, calcium phosphate is created on and around the charcoal in the sorbent suspension (the calcium and phosphorus concentrations in the blood are roughly equivalent to their levels when calcium phosphate is suspended in water and dissolves). Because of the calcium-phosphate solubility product, whenever blood phosphate levels fall, calcium phosphate dissolves and phosphate is released into the blood. Conversely, whenever blood calcium falls, the calcium phosphate dissolves and releases calcium, augmenting the return of calcium from the cation exchanger. Because changes in blood concentrations of calcium and phosphate are not likely to be quantitatively the same during hyperthermia, 10% calcium chloride solution is available, for infusion separately into blood returning to the patient as needed. The suspensions must be made carefully to assure that the calcium phosphate precipitate has maximal surface area for release or absorption of calcium or phosphate; forming the precipitate on the charcoal surfaces is one way to achieve this goal.

Also, when the above-described sorbent suspension dialyzer is used in conjunction with hyperthermia treatments, a blood pump must be added to the extracorporeal blood circuit in order to provide fast enough blood flow to effect the desired body heating in the time allotted. Fast blood flow is essential to the success of the hyperthermia treatment and its reversal. A blood pump is used to propel blood through a circuit containing a heat exchanger. In parallel to this circuit are inflow and outflow lines leading to the sorbent suspension dialysis system.

The membranes used for sorbent-based dialysis allow passage of all soluble chemicals under 5,000 molecular weight. The first function of hemodialysis with sorbent suspensions is to correct simple abnormalities in blood cationic electrolytes (known to vary during hyperthermic therapy) including sodium, potassium, calcium, magnesium and hydrogen (blood pH). This is achieved by loading the cation exchanger in the sorbent with sufficient cation amounts at equilibrium with the desired (normal) blood levels. If the blood concentration of a particular cation is lower than the equilibrium level, the cation will be released from the cation exchanger. If the blood concentration is above normal, the cation will be absorbed by the cation exchanger.

The cation exchanger of the sorbent suspension has some buffering effect to maintain normal blood pH. As a backup blood pH control, the pH of the sorbent suspension is monitored. If the sorbent pH becomes higher or lower than normal blood pH, an alarm sounds, and the user can direct the system to infuse acidic or basic solutions until the sorbent pH is the same as normal blood pH.

An exemplary sorbent suspension contains: 140 grams powdered activated charcoal; 22.1 grams $Na_2HPO_4*7H_2O$; and 3.0 grams $CaCl_2*2H_2O$ (added together, to the charcoal suspension); 200 grams Amberlite IRP-69 cation exchange resin loaded with blood equilibrium levels of Na, Ca, Mg and K ions; 13.0 grams NaCl; 15.1 grams $NaHCO_3$; and 1.5 grams of a glycol derivative and 1.5 grams of PVP to enhance stability and flow properties of the sorbent suspension. This is an example only, and is not intended to be limiting.

During hyperthermia, there may be other toxins which evolve, due to diminished kidney or liver function. The charcoal and cation exchangers in the sorbent suspension will remove many of these toxins, including: creatinine; aromatic amino acids; gamma-amino butyric acid; phenols; mercaptans; ammonium ion; nitric oxides; and various vasodilating hormones. Naturally, the sorbent suspension is not intended to remove proteins, intercellular messengers or cells, although to the degree that albumin-bound toxins can dissociate from albumin, these can also transfer across the membranes and be bound by the sorbents in the suspension.

Controlling plasma phosphate concentration is a little more complicated. In the body, calcium and phosphate concentrations are determined by their mathematical product. When the concentration of calcium in blood plasma goes up, calcium phosphate precipitates on bone and plasma phosphate level falls. Conversely, when plasma calcium concentration goes down, calcium phosphate is solubilized and plasma phosphate goes up. The present method invokes a system similar to the body's for phosphate concentration control, by creating a precipitate of calcium and phosphate on the large surface area of the charcoal (and in free suspension with the charcoal). When blood phosphate falls, the calcium phosphate dissolves to increase the free phosphate concentration in the sorbent suspension and transfer phosphate to the blood plasma. Conversely, if blood phosphate rises, phosphate can be removed from blood by precipitation of calcium phosphate in the sorbent suspension. The calcium-loaded cation exchanger moderates calcium concentration during these phosphate concentration changes. The sorbent suspension can be "tuned" to give more phosphate to all patients during treatment, by diminishing the amount of calcium added during the calcium phosphate precipitation step. Conversely, it can be "tuned" to give less phosphate to patients by adding more calcium in the calcium phosphate precipitation step.

When the subject matter of U.S. Pat. No. 5,277,820 is combined with the hyperthermia treatment described above, the main adaptations preferably include the addition of the blood pump discussed above and the use of various types of heating equipment to heat blankets over and underneath the patient, to heat the dialysate and directly to heat the blood through a heat exchanger. Most preferably, the sorbent suspension is maintained at 42° C., not 48° C., so that the blood tubing, dialyzer and sorbent suspension containers contact blood at modestly elevated temperature. The heat exchanger, final microfilter and the tubing returning blood to the patient will contact blood at a higher temperature (47°–48° C.), but these same components are used in open heart surgery to warm patients and safety of contact with blood of abnormal temperature has been thoroughly documented. It should be noted that this cautious approach was designed to expedite FDA approval, however, and that even when the sorbent suspension is heated to 48° C., no toxic reactions have occurred anywhere in the hyperthermia system.

FIG. 1 illustrates all of the cooperating elements for achieving the sorbent-based hemodialysis contemplated as a part of the present invention. The patient 10 is positioned on or between hyperthermia sources 12, which may be a heated mattress, a heated mattress with heated air emitting blanket, or a similar heat-imparting patient chamber. A blood outflow catheter 14 connects the patient to extracorporeal blood circuit tubing 18. The tubing 18 transports blood from blood outflow catheter 14 to a pump/heater control 20, through a pressure gauge 26 and to tubing which leads both to and past a sorbent-based hemodialyzer 30. The pump/heater control 20 and the sorbent-based hemodialyzer 30 are connected by a heater power line 22 and a heater temperature feedback control line 24, whereas the pump/heater control 20 and the pressure gauge 26 are connected by a pressure gauge feedback line 27. A hemodialyzer bypass control valve 28 is provided on the tubing passing the inlet and outlet of the sorbent-based hemodialyzer 30 to normally allow some of the blood to bypass the hemodialyzer when open, or to pass all blood through the dialyzer when closed. After the blood has passed through or past the hemodialyzer, it enters a heat exchanger 34 where it is heated, by heated water generated from a hyperthermia unit 36 and carried through hyperthermia unit heater lines 38. The hyperthermia unit 36 also provides heat to the hyperthermia sources 12 via hyperthermia unit heater lines 38. After the blood is heated in heat exchanger 34, it passes through temperature gauge 32 and flows back to the patient 10 past a blood sample port 40. Air bubbles are removed from the blood in a drip chamber and micro bubble filter 42 located between sample port 40 and a blood return catheter 44. The blood outflow catheter 14 and blood return catheter 44 may be separate arterial and venous catheters or a single, double-lumen structure, both of which are well-known in the art. Regardless of how catheters 14 and 44 are configured, they are connected by a bypass control valve 16 to provide the option of immediate return of blood to the patient, should need arise, without the blood's travelling through the entire extracorporeal circuit. The pump/heater control 20 imparts some heat to the blood through heating the sorbent suspension but preferably does not raise the sorbent suspension temperatures above about 42° C. In this way, heat loss from the blood is avoided when body core temperature increases to 42° C.

Blood flow rates of 300–600 ml/minute are preferred, with a maximum blood flow rate of 800 ml/minute. "Roller pumps" or centrifugal pumps capable of achieving these blood flows are known in the art, and typically are the same pumps used for heart perfusion during so-called "open heart" surgery. Referring once again to FIG. 1, such a roller pump appears as the pump/heater control 20.

When the sorbent-based hemodialysis is used, the sorbents clear approximately 50% of the sedative from the bloodstream. Therefore, administration of approximately twice the dosage of sedative will give the same sedative effect as when standard dosage is used.

Besides the current ability to control a number of blood chemistry values, some modifications of the sorbent suspension could control other chemistries. If the sorbent suspension were loaded with a sedative such as thiopental sodium to be in equilibrium with a level causing sedation, then the blood level quickly rises to this concentration when the patient is placed on hyperthermia. Further sedation can be created by administering an injection of thiopental sodium to the blood; the pre-loaded sorbent suspension would not remove significant amounts of the drug. If any organic chemical were found to augment the effects of hyperthermia on HIV, it could be loaded into the sorbent suspension and delivered during treatment to maintain a reasonably constant blood concentration.

The invention may be further illustrated by means of the following examples.

EXAMPLE 1

Animal Studies

A. Normal Calves

Tests were performed to determine the safety of WBHT. These animal experiments were performed with the apparatus depicted in FIG. 1, except that no heating blanket was employed. The sorbent temperature at 44° C. during the treatments. Nine normal Holstein calves, average weight 70 kilograms, were sedated with Rompun to a level which caused a slow but regular respiratory rate. If respirations became slow and irregular, the animals were intubated and placed on mechanical ventilation (this was necessary in 3 animals). By dissection, 16 French cannulas were inserted in the carotid artery and vein, an intra-arterial temperature probe was placed through the carotid artery, and another temperature probe was placed in the esophagus. The treatment raised the core temperature to 42° C. for 35∝55 minutes; the animals were then cooled to normal blood temperature. Blood chemical values and cellular counts were measured frequently during the treatment. After treatment, the catheters were removed, the incisions closed, and the animals allowed to awaken. The animals were observed for the next 30 days, and had blood tests drawn each week. No prophylactic antibiotics were administered to the animals.

All of the animals achieved 42° C. core temperature, and all survived the hyperthermic procedure. None of these animals developed evidence of bleeding tendency or DIC.

Slight increases in SGOT and SGPT occurred in all animals, and an increase in alkaline phosphatase occurred in six animals. Serum potassium increased slightly in a few animals, due to the fact that potassium was added to the calcium chloride in the replacement fluid. No calf died within 24 hours of the procedure. One died 14 days after the procedure, due to pneumonia (confirmed by autopsy). This complication might have been avoided if prophylactic antibiotics were administered. Another calf expired 28 hours after the treatment from pulmonary edema (confirmed by autopsy, with no other pathological changes noted in any organ). Each of these calves had been intubated and placed on a respirator during WBHT. Evaluation of the treatment of this calf led to the conclusion that if fluid replacement had been performed according to a protocol to maintain pulmonary wedge pressure or central venous pressure at normal levels, acidosis and hypotension would have been prevented, as well as the cardiac damage which eventually led to pulmonary edema.

These animal studies, performed with minimal cardiovascular monitoring, indicate that the treatment is generally safe, with all animals surviving the procedure and two late complications. Administering fluids according to the need, as indicated by Swan-Ganz catheter, careful antisepsis techniques during catheter placement, and administration of prophylactic antibiotics would have diminished the animal mortality of this study to zero.

B. Pig

An animal study was designed to closely monitor the chemical changes which occur during WBHT treatment. In this study a normal pig of 20 kg weight was treated in accordance with the general procedure in Example 1(A), with sorbent temperatures of 48° C. to provide a more strenuous test for the equipment, blood and subjects. After sedation with Rompun, the pig was intubated and allowed to breathe naturally. Temperature monitors were placed in the esophagus, bladder, and rectum. By surgical cutdown, 8 French catheters were placed in femoral artery and femoral vein, and a Swan Ganz catheter placed in the pulmonary artery. The apparatus was attached to the femoral artery and vein catheters, blood flow was set at 450 ml/min, and within 30 minutes the core temperature of the animal reached 42° C.

Blood sodium and potassium concentrations remained normal during the procedure. Blood calcium and magnesium concentrations remained normal during the procedure, while an abnormally elevated phosphorus level fell towards normal during the procedure. The results demonstrate that when the apparatus of the invention is used in WBHT, blood chemistries either remain normal or become more normal.

C. Simian Immunodeficiency Virus (SIV)-infected Rhesus Monkey

SIV is a retrovirus highly similar to HIV in its physical characteristics and in its effects on the body. To investigate the effect of WBHT on primates with this infection, an 8 kilogram Rhesus monkey infected with SIV was treated according to the general procedure of Example 1(A). The sorbent temperature was 48° C.

The animal was anesthetized and intubated, and 8 French catheters were placed in the femoral artery and vein. A Swan-Ganz catheter was placed, and fluid management was according to the protocol for human treatments. The apparatus was attached to the femoral catheters, and blood treatment rate set at 200 ml/min (a high rate, considering the small size of the animal). Within one hour the core temperature of the monkey reached 42° C. and this core temperature was maintained for one hour. Blood sodium and potassium concentrations remained normal during and after the treatment. Calcium and magnesium remained normal during and after the treatment, though phosphorous declined during the treatment (leveling out probably due to phosphate replacement from the sorbent). Blood pH was maintained at a normal value in spite of slightly falling $pCO_2$ and $HCO_3$ levels. Urine output remained relatively constant during the treatment, and increased after the treatment. There was an immediate drop in hematocrit at the start of the treatment (due to dilution of the blood volume by the extracorporeal circuit volume), but the hematocrit remained stable during the rest of the treatment.

Blood drawn before and after the treatment indicated no change in liver enzymes, creatinine, electrolytes or other laboratory values. There was a drop in albumin concentration and platelet count, partly accounted for by dilution of blood by the volume of the extracorporeal circuit, and by the huge surface area of the circuit relative to the animal's size.

The monkey survived the treatment and was returned to his cage shortly after the procedure, in good health. On the first day after treatment, the animal appeared in good health. On the second day after treatment, the animal was found in the cage without pulse or respiration, still warm. An autopsy was performed, which showed no macroscopic or microscopic pathology of any organ system, and no signs of significant internal bleeding (in spite of a drop in blood platelet concentration during the treatment). Dr. James Blanchard, director of the Tulane Primate Center, reviewed all data related to the case and stated in a letter that the death of the animal "was not related any side-effect of the treatment," even though it was not clear just what caused the death. Tissue samples were submitted for determination of viral load by the limiting dilution PCR test. Compared to titers determined on tissue just before the treatment, the viral load had diminished from a titer of 1:64 to 1:32. Though this change is not statistically significant, it is impressive, given the short time between treatment and measurement of the titer.

EXAMPLE 2

Treatment of HIV-Infected Patients with KS

Two patients with HIV infection and Kaposi's Sarcoma were treated as follows. The treatments were performed in Santo Domingo, under approval of the Director of the Ministry of Health. Screening techniques were as follows. A pre-operative evaluation included: biopsy of any existing Kaposi's Sarcoma lesion; complete blood cell count; biochemical profile; electrolytes; antigen P24; reverse transcriptase assay; western blot; human immunodeficiency virus antibody; immunoglobin assay; lymphocyte fractions (including $CD_4$); coagulation studies; spirometry; and echocardiogram. Patients were selected for treatment in this study if they were between the ages of 18 and 40, tested positive for the human immunodeficiency virus, had Kaposi's Sarcoma as a result of HIV, and had normal or at least 80% normal pulmonary, cardiac, renal and hepatic functions. (Patients were excluded from this study if they exhibited severe immunodepression, extensive Kaposi's lesions in vital organs, were at cardiac risk or had had radiation of the mediastinum or vital organs.)

The first patient was a 38 year old male having had known HIV infection for about four years. In 1989 he developed numerous nodular, red-violet colored lesions on both feet, the abdomen and the back. Biopsies in 1989 and 1993 confirmed the lesions to be Kaposi's Sarcoma. The leg lesions, which bothered the patient the most, had previously been irradiated many times, but had only partially responded. The largest lesion, on the dorsum of the right foot was quite painful and tender, and developed during 1993. Other symptoms of HIV included diarrhea and weight loss, though the patient's physical examination was normal and he appeared reasonably able to complete daily activities. He had not taken any medications for HIV infection, but had taken antibiotics intermittently.

Treatment was performed with the apparatus illustrated in FIG. 1, with a sorbent suspension temperature of 48° C. Access was established using an ultrasound-guided needle under local anesthesia, and the following were positioned: a 7 French Swan-Ganz catheter through a femoral vein (and advanced into the pulmonary artery); an 18 gauge catheter in a femoral artery for arterial pressure monitoring; a 10 French catheter in a femoral artery; and a 10 French catheter in a femoral vein. Through a peripheral vein, 100 mg thiopental sodium was administered, and the procedure begun. The patient was given 4000 units of heparin at the start of the procedure, and 2 mg of dexamethasone, as planned. By blood clotting tests, the patient required one more injection of 2000 units of heparin during the treatment. Fluid replacement in the patient was effected according to the skill of the art, to keep the wedge pressure constant at its starting value; 3 liters of normal saline were administered total. A total of 700 mg thiopental sodium was administered during the procedure. Calcium chloride infusion to blood was made at the rate of 5 ml/hour.

Blood flow in the extracorporeal circuit was begun at a rate of 500 ml/minute, and was increased slowly to 600 ml/minute. The sorbent suspension contained 140 grams powdered activated charcoal; 22.1 rams $Na_2HPO_4*7H_2O$; 12.2 grams $CaCl_2*2H_2O$; 100 grams Amberlite IRP-69 cation exchange resin loaded with blood equilibrium levels of Na, Ca, Mg and K ions; 8.8 grams NaCl; 15.1 grams $NaHCO_3$; and 3 grams of a glycol derivative to enhance stability and flow properties of the sorbent suspension, and its temperature remained stable at 48° C. during the treatment (as did the water temperature), and the temperature of blood leaving the heat exchanger reached nearly 47° C. When esophageal and rectal (core) temperature reached 42° C., the water temperature was decreased from 48° C., and the exiting blood temperature dropped to 45° C. (while core temperature remained constant). It was pre-planned that the patient would be heated to a core temperature of 42° C. for only a half hour's duration, so the cool-down period was begun at 90 minutes of treatment. The procedure ended 140 minutes after it had begun, and all catheters were removed (except the Foley catheter—left in place for post-procedure urine collection). Encyclopedic records of blood levels and organ functions were kept throughout the procedure.

The patient's antigen status by PCR changed 4 weeks post treatment, from positive to negative, indicating a decrease in viral load in body and blood. The morning after the procedure the patient stated he had no pain and was "filled with vigor" and felt great. Over the course of the first post-procedural week, the largest lesion, on the right foot, decreased 50% in size and by two weeks post treatment the lesion had only 25% of its original size and was much less tender and painful. It remained so at 8 weeks post procedure.

The second patient was a 28 year old patient who had become HIV positive about three years earlier. Beginning in December of 1992, he developed black to purplish lesions on his right arm, then on his left arm, then over his entire body including forearms, legs, chest, nose and face. Biopsy proved the lesions to be Kaposi's Sarcoma. Therapy in 1993 included radiation which only made the lesions look slightly less dark and did not change the size at all. Intra-lesion injections of cytotoxins made the lesions more solid. The patient had taken AZT but had quit, not perceiving any benefit. Though the patient exercised frequently and ate well, he had lost 25 pounds in the preceding year, dropping from 145 to 120 pounds.

Treatment was performed, again with a 48° C. sorbent suspension temperature, according to the same protocol described for the first patient except with minor adjustments in dosages. Patient wellbeing improved according to the patient's comments post procedure, and the Kaposi's Sarcoma lesions faded. The patient gained 5 pounds and maintained this weight.

Although the invention has been described with particularity above, it is to be limited only insofar as is set forth in the accompanying claims.

We claim:

1. A method for the extracorporeal heating of blood in a patient having veins and arteries for the flow of blood in which extracorporeal hyperthermia is indicated, comprising the steps of:

creating an extracorporeal blood circuit;

catheterizing one of said veins or said arteries;

connecting said catheterizing vein or artery to said extracorporeal blood circuit, whereby blood flows from said vein or artery into said circuit;

heating at least some of the blood in said extracorporeal blood circuit to a temperature of at least 46° C. by a primary heating means;

subjecting at least some of the blood in said extracorporeal blood circuit to hemodialysis; and returning said heated blood to the patient.

2. The method according to claim 1 wherein said heating step further comprises heating at least some of the blood in said extracorporeal blood circuit by elevating the temperature of a dialyzing solution used in the hemodialysis step.

3. The method according to claim 2 wherein said heating step further comprises heating at least some of the blood in said extracorporeal blood circuit by elevating the temperature of the blood directly with a heat exchanging means.

4. The method according to claim 1 wherein said heating step further comprises heating at least some of the blood in said extracorporeal blood circuit to raise the core temperature of the patient to approximately 41.5°–42° C.

5. The method according to claim 1 wherein said extracorporeal blood circuit includes a blood pump.

6. The method according to claim 5 wherein said blood pump is upstream of a means for effecting said hemodialysis, and including a supplemental heating means associated with said blood pump.

7. The method according to claim 6 wherein said hemodialysis is effected by means of a hemodialyzer containing at least one dialysis membrane and a sorbent suspension.

8. The method according to claim 7 wherein said heating step further includes heating the body of the patient with a heated mattress.

9. The method according to claim 8 wherein said heating step further includes heating the body of the patient with a heated blanket.

10. The method according to claim 9 wherein said extracorporeal blood circuit contains a heat exchanger downstream of said hemodialyzer.

11. A method for treating a neoplasm in a patient, comprising the steps of heating and dialyzing the blood of said patient, wherein the blood of the patient is heated for a period of time to at least 46° C.

12. The method according to claim 11 wherein said heating effects whole body hyperthermia to a core body temperature of 41.5°–42° C.

13. The method according to claim 12 wherein said dialyzing is accomplished by means of sorbent suspension containing a water suspension of 140 grams powdered activated charcoal; 22.1 grams $Na_2HPO_4*7H_2O$; 12.2 grams $CaCl_2*2H_2O$; 100 grams cation exchange resin loaded with Na, Ca, Mg and K ions; 8.8 grams NaCl; 15.1 grams $NaHCO_3$; and 3 grams of a glycol derivative.

14. A method for treating a viral infection in a patient, comprising the steps of heating and dialyzing the blood of said patient, wherein the blood of the patient is heated for a period of time to at least 46° C.

15. The method according to claim 14 wherein said heating effects whole body hyperthermia to a core body temperature of 41.5°–42° C.

* * * * *